United States Patent

Furuie

[11] Patent Number: 5,825,477
[45] Date of Patent: Oct. 20, 1998

[54] APPARATUS FOR MEASURING PARTICLE MORPHOLOGY AND METHOD THEREOF

[75] Inventor: Dai Furuie, Kobe, Japan

[73] Assignee: TOA Medical Electronics Co., Ltd., Hyogo, Japan

[21] Appl. No.: 771,415

[22] Filed: Dec. 20, 1996

[30] Foreign Application Priority Data

Dec. 22, 1995  [JP]  Japan .................................. 7-335329

[51] Int. Cl.⁶ .............................. G01N 21/00; G01N 5/02
[52] U.S. Cl. ................................. 356/72; 356/335
[58] Field of Search .......................... 356/39–40, 72–73, 356/335; 250/564, 573, 576

[56] References Cited

U.S. PATENT DOCUMENTS

| | | | |
|---|---|---|---|
| 4,198,160 | 4/1980 | Kachel et al. | 356/317 |
| 4,298,836 | 11/1981 | Groves et al. | 324/71.1 |
| 4,338,024 | 7/1982 | Bolz et al. | 356/39 |
| 4,510,438 | 4/1985 | Auer | 356/72 |
| 4,515,274 | 5/1985 | Hollinger et al. | 356/39 |
| 5,088,816 | 2/1992 | Tomioka et al. | 356/39 |
| 5,138,181 | 8/1992 | Lefevre et al. | 356/73 |
| 5,194,909 | 3/1993 | Tycko | 356/40 |
| 5,506,673 | 4/1996 | Kosaka et al. | 356/72 |

FOREIGN PATENT DOCUMENTS 0652428  5/1995  European Pat. Off. .

Primary Examiner—Frank G. Font
Assistant Examiner—Jason D. Vierra-Eisenberg

[57] ABSTRACT

A particle measuring apparatus includes a resistance detecting section for converting a sample solution containing particles into sample flow to detect an electric resistance thereof, an image capturing section for converting the sample solution into a flat flow to capture an image of the flat flow on a wider side thereof to obtain a particle image, and an analyzing section for analyzing a particle on the basis of the detected electric resistance and the captured particle image, the analyzing section including a first detecting section for detecting information on a volume of each particle from the detected electric resistance, a second detecting section for detecting information on a projected area of each particle from the captured particle image, a depth calculating section for calculating information on a depth dimension of the particle by using a first particle size distribution calculated on the basis of the information on the volume and a second particle size distribution calculated on the basis of the information on the projected area, and an output control section for causing an output section to output the information on the depth dimension and the captured particle image.

13 Claims, 9 Drawing Sheets

APPARATUS FOR MEASURING PARTICLE MORPHOLOGY AND METHOD THEREOF

BACKGROUND OF THE INVENTION

1. Field of the Invention

The present invention relates to a particle measuring apparatus and method, and more particularly to an apparatus for measuring a shape and depth dimension of powder particles, and a method thereof.

2. Description of the Related Art

It is very important to analyze and measure the shape and depth dimension of each particle in order to control the quality of fine particles such as fine ceramics particles, pigments, powders for cosmetics, toners, and the like.

An imaging flowcytometer has been widely used for capturing an image of each particle of a particle containing sample solution and obtaining the shape and area of the particle to be analyzed (for example, see U.S. Pat. Nos. 4,338,024 and 5,088,81). Further, a measuring apparatus using an electrical sensing zone method is used for converting the particle containing sample solution into a flow enveloped in a sheath solution, detecting change of an electric resistance of the flow which is obtained when the particle in the flow passes through an orifice, irradiating light onto the flow to detect an intensity of scattered light generated from the particle, and calculating each volume of the particles on the basis of a result of detection (for example, see European Unexamined Patent Publication No. 52428A1).

However, such imaging flowcytometer and measuring apparatus are not adapted to measure information on depth dimension of particles.

SUMMARY OF THE INVENTION

In consideration of these circumstances, it is an object of the present invention to provide an apparatus for functionally combining an imaging flowcytometer and an apparatus using an electrical sensing zone method to statistically measure a shape and depth dimension (thickness) of particles, and a method thereof.

The present invention provides a particle measuring apparatus, comprising a first flow cell for converting a particle containing sample solution into a sample solution flow enveloped in a sheath solution, a resistance detecting section for detecting an electric resistance of the sample solution when the sample solution flows in the first flow cell, a second flow cell for converting the particle containing sample solution into a flat flow enveloped in the sheath solution, an image capturing section for capturing an image of the flat flow on a wider side thereof to obtain a particle image when the sample solution flows in the second flow cell, an analyzing section for analyzing particles on the basis of the detected electric resistance and the captured particle image, and an output section for outputting a result obtained from the analyzing section, the analyzing section including a first detecting section for detecting information on a volume of each particle from the detected electric resistance, a second detecting section for detecting information on a projected area of each particle from the captured particle image, a first particle size distribution calculating section for calculating a first particle size distribution on the basis of the information on the volume, a second particle size distribution calculating section for calculating a second particle size distribution on the basis of the information on the projected area, a depth calculating section for calculating information on a depth dimension of the particle on the basis of the first and second particle size distributions, and an output control section for causing the output section to output the information on the depth dimension an , the captured particle image.

DESCRIPTION OF PREFERRED EMBODIMENTS

Figure 1:
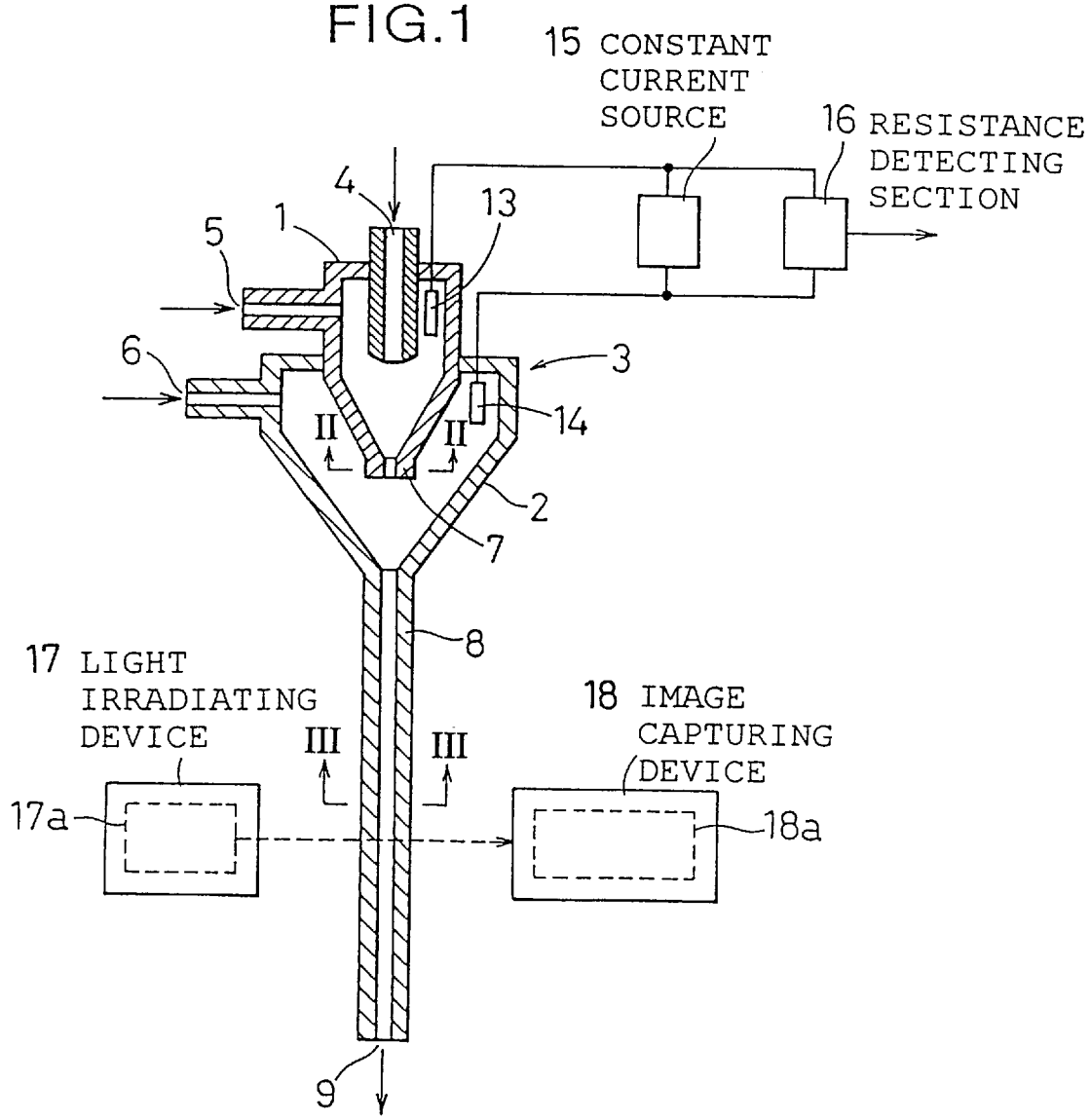
FIG. 1 is a sectional view showing main parts according to an embodiment of the present invention.

Examples of particles to be analyzed by an apparatus according to the present invention include inorganic fine particles such as fine ceramics, pigments, powders for cosmetics and toner, organic fine particles such as food additives, bioparticles such as blood corpuscle, and particles which are dyed by a dye or labeled reagent in advance. It is preferable that particles to be analyzed have a size of 5 to 400 $\mu$m. Even if the particle to be analyzed has a size which is more than 400 $\mu$m, it can be analyzed by increasing the size of the pore of first and second flow cells.

The first flow cell according to the present invention is formed of a cell which communicates with the pore (orifice) and houses an electrolyte, and more suitably, envelops a particle containing sample solution in a sheath solution to form a flow of the sample solution by hydrodynamic effects so that the particle can pass through the pore in a line.

The first flow cell used for the present invention can cause the sample solution to flow through a pore having a diameter of 20 to 1000 $\mu$m at a speed of 0.5 to 10 m/sec, for example.

Furthermore, it is preferable the sheath solution is beforehand prepared so that the sample solution is equivalent to the sheath solution in conductivity.

It is preferable that the resistance detecting section includes first and second electrodes provided in the first flow cell with a pore interposed therebetween, a power supply for applying a voltage between the first and second electrodes, and a detecting device for detecting, as an electric resistance signal, a current which flows between the first and second electrodes or a voltage therebetween in order to detect change of an electric resistance between the first and second electrodes when the particle passes through the pore.

The electric resistance signal has an angle pulse shape when the particle passes through the pore. As is well known, a height of a pulse is almost proportional to a volume of the particle.

The second flow cell can envelop the flow of a particle containing sample solution, that is, a particle suspension in a sheath solution to convert the same flow into a flat flow by hydrodynamic effects. A well-known cell can be used for the second flow cell.

The second flow cell includes a passage (an orifice) through which the flat flow having a width of 1000 to 10000 $\mu$m and a thickness of 100 to 1000 $\mu$m can be defined, for example.

It is preferable that the kind of the sheath solution supplied to the second flow cell is selected corresponding to the characteristics of the particle suspension (those of particles and a solvent).

Preferably, the first flow cell is incorporated with the second flow cell in series. However, they may be arranged in parallel.

The image capturing section may include a light irradiating device and an image capturing device. It is preferable that a stroboscope for emitting a pulse and a laser beam source are used for the light irradiating device. A light source for continuously emitting light can also be used. In this case, however, a shutter should be provided on the image capturing device. A general video camera (CCD camera) for capturing two-dimensional images can be used for the image capturing device.

Preferably, the light irradiating device and the image capturing device are provided with the second flow cell interposed therebetween, and the light irradiating device irradiates light orthogonally to a flat face of the particle suspension flow and the image capturing device is provided on an optical axis thereof in the case where the particle suspension flow is converted into the flat flow in the second flow cell.

It is preferable that an analyzing section is formed of a microcomputer including a CPU, a ROM, a RAM, and an I/O port.

For example, a CRT, a liquid crystal display and a printer can be used for the output section.

The analyzing section according to the present invention detects a maximum projected image of the particle and a depth dimension thereof to be outputted from the output section. The principle of detection will be described below.

Figure 9:
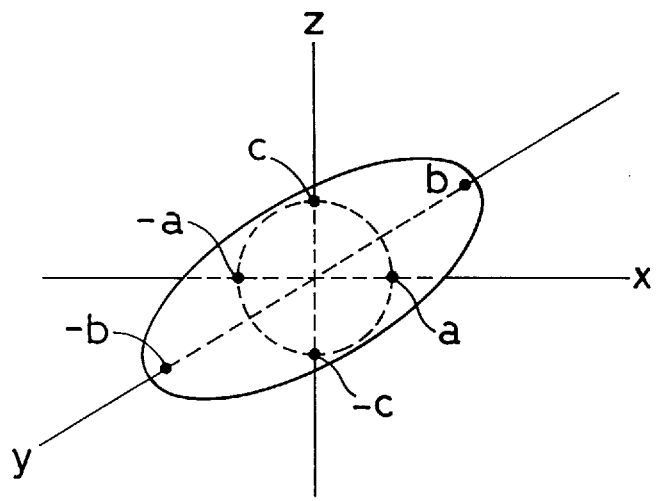
FIG. 9 is a chart showing an example of a particle shape measured by the present invention.

Assuming that the particle is ellipsoidal as shown in FIG. 9, the particle is represented by the following equation:

$$(x^2/a^2)+(y^2/b^2)+(z^2/c^2)=1, (a<c<b).$$

In consideration of an orientation of the particle, an image of the particle is captured in an x-axis direction. An area of the particle image (maximum projected area) is represented by S and a volume thereof is represented by V in the following equation.

$$S=\pi bc \quad (a)$$

$$V=\pi \cdot abc/3 \quad (b)$$

The orientation of the particle will be described below. It has been well known that a shearing force always acts on the particle which flows in a liquid. The shearing force acts on the particle so that a direction of the particle is changed in the flow such that a resistance is reduced. The second flow cell controls the sample solution to always have a flat flow.

A greater shearing force acts on the particle which flows in the sample solution in a direction of a minor axis of the flat flow. Therefore, the particle flows flatly such that a greater area is always parallel with a direction of a major axis of the flow. By capturing the image of the particle in the flow on a wider side thereof so as to be parallel with the major axis direction of the flow, a particle image having a maximum projected area can be captured.

Assuming that the area S is equal to an area of a circle having a diameter Rs and the volume V is equal to a volume of a sphere having a diameter Rv, a circle equivalent diameter Rs and a sphere equivalent diameter Rv are represented by the following equations obtained from the equations (a) and (b).

$$Rs=2(bc)^{1/2} \quad (1)$$

$$Rv^3=8abc \quad (2)$$

The following equation (3) is obtained from the equations (1) and (2).

$$R=Rv^{3/2}/(2a)^{1/2} \quad (3)$$

Because of a <c <b, the following equation (4) is obtained.

$$a<(bc)1/2 \quad (4)$$

The following equation (5) is obtained from the equations (4) and (1).

$$Rs>2a \quad (5)$$

The following equation (6) is obtained from the equations (5) and (3).

$$Rs>Rv \quad (6)$$

Figure 10:
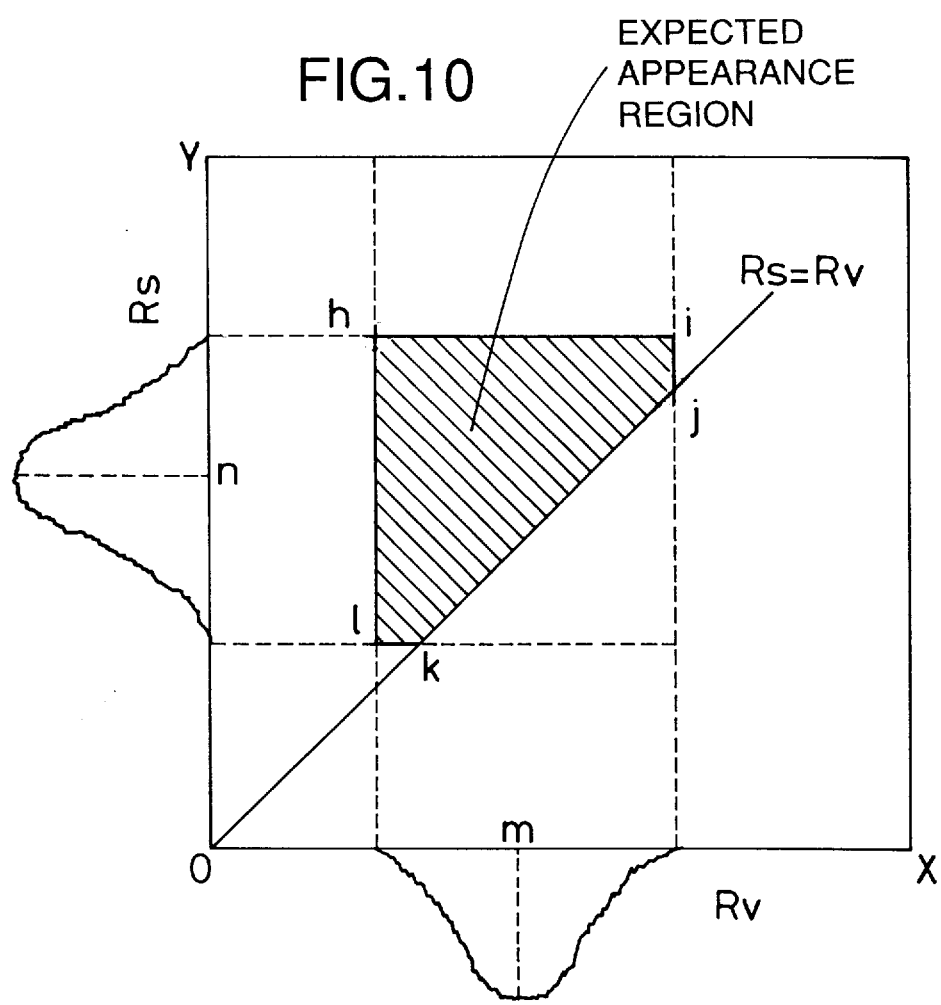
FIG. 10 is a graph showing a comparison between particle size distribution data according to the present invention.

A first particle size distribution obtained by a first particle size distribution calculating section, that is, a particle size distribution related to the sphere equivalent diameter Rv is compared with a second particle size distribution obtained by a second particle size distribution calculating section, that is, a particle size distribution related to the circle equivalent diameter Rs on X-Y coordinates as shown in FIG. 10. Consequently, an expected appearance region of the particle on the X-Y coordinates is a region provided on an upper side of a straight line Rs=Rv, that is, a region enveloped in a pentagon hijkl on the basis of relationship in the equation (6).

As shown by the equation (3), Rs represents a monotone increasing function of Rv. On the coordinates shown So in FIG. 10, "a" has a maximum value when a curve of the equation (3) passes through a point j, and has a minimum value when the curve of the equation (3) passes through a point h.

Accordingly, coordinates of the points j and h are substituted for the equation (3) respectively so that maximum and minimum values of a depth dimension (2a) of the particle are calculated. If mean values of the first and second particle size distributions are m and n as shown in FIG. 10, they are substituted for the equation (3) so that a mean value of the depth dimension of the particle can be obtained.

From another viewpoint, the present invention provides a method for measuring a particle, comprising the steps of converting a particle containing sample solution into a sample flow enveloped in a sheath solution, detecting information on a volume of each particle in the sample flow, converting the sample flow into a flat flow enveloped in the sheath solution, capturing an image of the flat flow on a wider side thereof to obtain a particle image, detecting information on a projected area of each particle from the captured particle image, calculating a first particle size distribution on the basis of the information on the volume, calculating a second particle size distribution on the basis of the information on the projected area, calculating information on a depth dimension of the particle based on the first and second particle size distribution, and outputting the information on the depth dimension and the captured particle image.

These and other objects, features, aspects and advantages of the present invention will become more apparent from the following detailed description of the present invention when taken in conjunction with the accompanying drawings.

The present invention will be described below in detail according to the preferred embodiment with reference to the drawings. The present invention should not be construed as being limited by the following embodiment.

Figure 2:
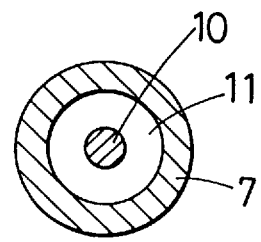
FIG. 2 is a sectional view seen in a direction of an arrow II—II shown in FIG. 1.

FIG. 1 is a sectional view showing main parts according to an embodiment, in which a composite flow cell 3 having a first flow cell 1 and a second flow cell 2 coupled integrally includes an injection port 4 for injecting a particle containing sample solution, an injection port 5 for injecting a first sheath solution, an injection port 6 for injecting a second sheath solution, and an orifice 7 for enveloping, in a first sheath solution 11, the particle containing sample solution injected from the injection port 4 as shown in FIG. 2 to cause particles to pass in a line.

Figure 3:
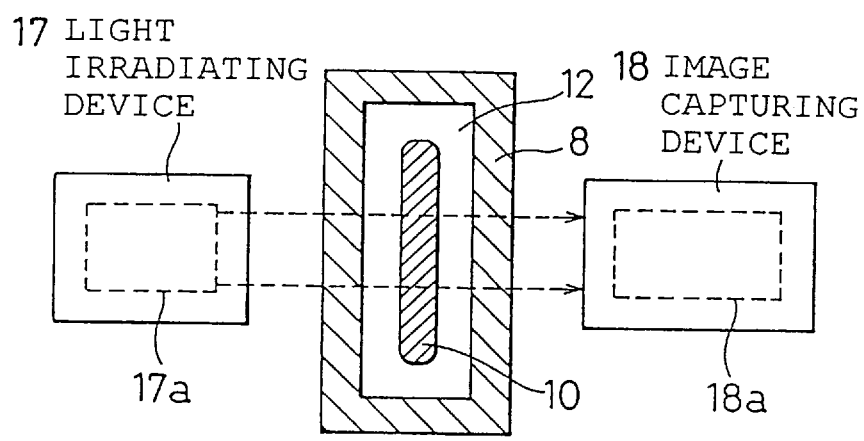
FIG. 3 is a sectional view seen in a direction of an arrow III—III shown in FIG. 1.

Furthermore, the flow cell 3 includes an orifice 8 for enveloping, in a second sheath solution 12, a sample solution 10 which has passed through the orifice 7 as shown in FIG. 3, and for converting a flow of the solution into a flat flow, and a discharge port 9 for discharging the first and second sheath solutions 11 and 12 and the particle containing sample solution.

FIG. 2 is a sectional view seen in a direction of an arrow II—II shown in FIG. 1, and FIG. 3 is a sectional view seen in a direction of an arrow III—III shown in FIG. 1. At the orifice 7, the flow of the sample solution 10 is reduced by the first sheath solution 11 as shown in FIG. 2. Consequently, particles contained in the sample solution 10 pass through the orifice 7 in a line.

First and second electrodes 13 and 14 made of platinum are provided in the flow cell 3. A constant current source 15 is connected to the first and second electrodes 13 and 14. For this reason, a voltage between the electrodes 13 and 14 is varied every time the particles pass through the orifice 7. A resistance detecting section 16 detects change of a resistance between the electrodes on the basis of a voltage between the electrodes 13 and 14.

At the orifice 8, the flow of the sample solution 10 is converted into the flat flow by the second sheath solution 12 as shown in FIG. 3.

A light irradiating device 17 and an image capturing device 18 are provided with the flow cell 3 interposed therebetween. The light irradiating device 17 irradiates light orthogonally to a flat face of the flat flow by the orifice 8, and the image capturing device 18 is provided on an optical axis thereof. The light irradiating device 17 includes a stroboscope 17a, and the image capturing device 18 includes a video camera 18a.

Pulse light is periodically irradiated from the stroboscope 17a onto the flat flow every 1/30 sec. Consequently, static images of the particles are captured by the video camera 18a every 1/30 sec.

If the flat face of the flat flow is captured by the video camera 18a, the particle image can be captured over the whole image capturing area of the video camera 18a. Images of a lot of particles can be captured at a time.

A distance between a center of gravity of the particles whose images are captured and the image capturing face of the video camera 18a is almost constant. Consequently, it is possible to always obtain particle images which are in focus irrespective of a size of the particle. Furthermore, flat or slender particles are deflected by hydrodynamic effects in a direction in which a resistance is the smallest. Therefore, the particle image which is obtained represents a maximum projected area of the particle.

The number of the particle images which are captured by irradiating pulse light plural times is determined depending on the image capturing area of the video camera 18a, the thickness of a sample flow, the number of particles of a particle suspension per unit volume, and the number of image capturing operations (the number of frames).

Figure 4:
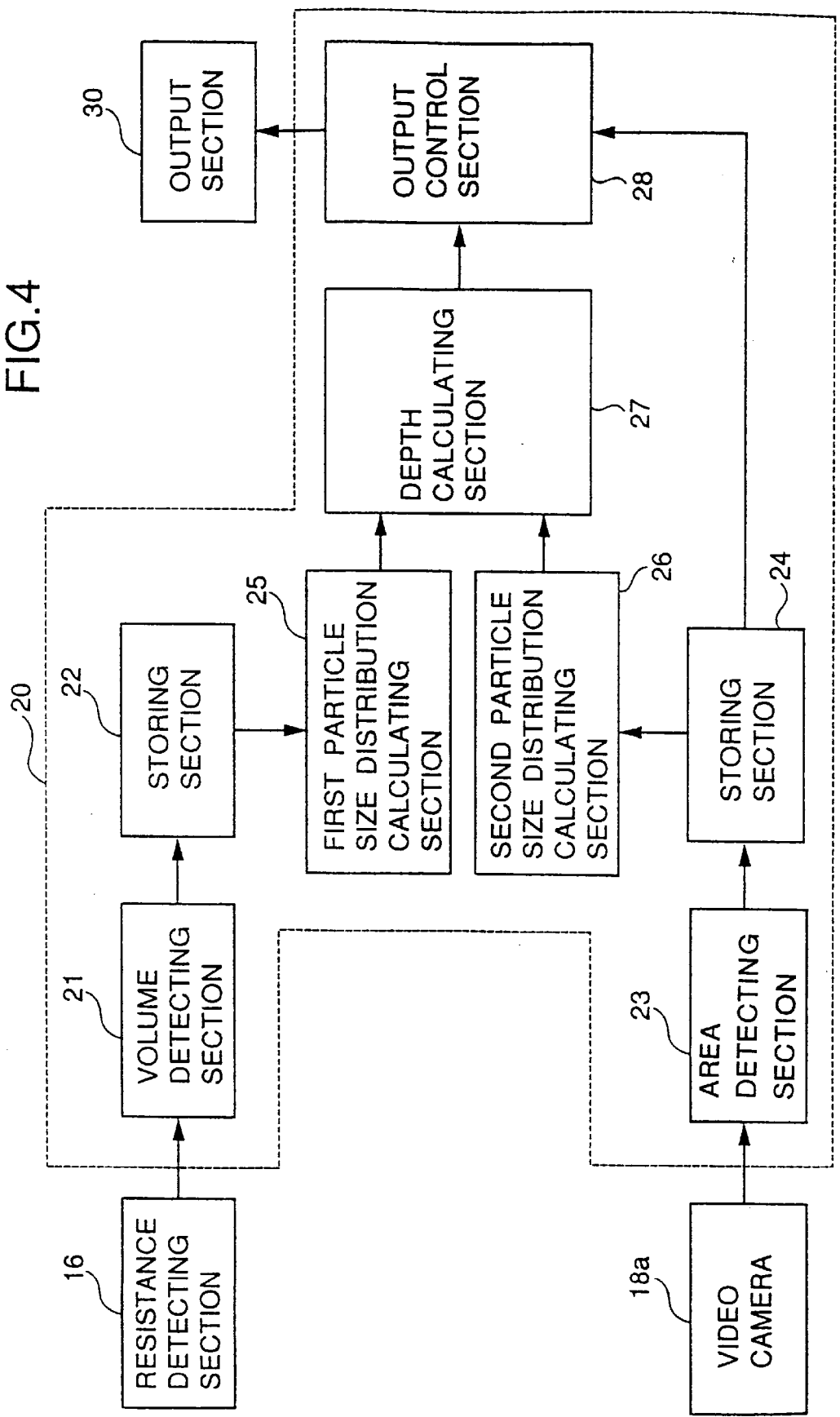
FIG. 4 is a block diagram showing the embodiment according to the present invention.

FIG. 4 is a block diagram showing an analyzing section 20 according to the present embodiment. A volume detecting section 21 detects the volume of each particle which passes through the orifice 7 on the basis of a signal sent from the resistance detecting section 16, and stores a result of detection in a storing section (RAM) 22.

An image signal outputted from the video camera 18 is A/D converted by an area detecting section 23, and fetched as image data. Then, background correction is performed to correct an uneven intensity (shading) of the light irradiated onto the sample solution flow. Thereafter, the image data is converted into binary on a suitable threshold level. Thus, the maximum projected area of the particle is calculated from the total number of pixels of each particle.

Furthermore, the area detecting section 23 cuts the particle image from the frame in which the image is captured. The cut particle image is stored in a storing section (RAM) 24 together with the value of the maximum projected area.

A first particle size distribution calculating section 25 reads out a volume of each particle from the storing section 22 to calculate a sphere equivalent diameter Rv of each particle and calculate a frequency distribution for the sphere equivalent diameter Rv, that is, a first particle size distribution.

A second particle size distribution calculating section 22 reads out a maximum projected area of each particle from the storing section 24 to calculate a circle equivalent diameter Rs of each particle and calculate a frequency distribution for the circle equivalent diameter Rs, that is, a second particle size distribution.

A depth calculating section serves to find an expected appearance region of the particle by comparing the first and second particle size distributions which are calculated as shown in FIG. 10, and to calculate information on a depth dimension of the particle, that is, a maximum depth dimension, a minimum depth dimension and a mean depth dimension on the basis of the expected appearance region.

An output control section 28 causes an output section 30 to output information on the depth dimension, the first and second particle size distributions and the like together with particle images stored in the storing section 24.

Each of the first and second particle size distribution calculating sections 25 and 26 calculates a cumulative particle size distribution, a 10% diameter, a 50% diameter and a 90% diameter, and causes the output section 30 to output a result of calculation through the output control section 28. The 10% diameter, 50% diameter and 90% diameter indicate particle diameters whose cumulative particle size distributions have values of 10%, 50% and 90%. In other words, the 50% diameter is a central value of a particle size, and is also referred to as a median diameter.

EXAMPLE

An example according to the above-mentioned embodiment will be described below.

Carbon which acts as a particle to be measured is mixed with an electrolyte to prepare a particle containing sample solution. The electrolyte is used for a first sheath solution and a second sheath solution. The carbon has a nominal particle size (sphere equivalent diameter) of 4 μm.

In a flow cell 3, a passage of an orifice 7 is a circular hole having an inner diameter of 100 μm, and that of an orifice 8 has a square hole having a size of 4000 μm ×1000 μm.

Figure 5:
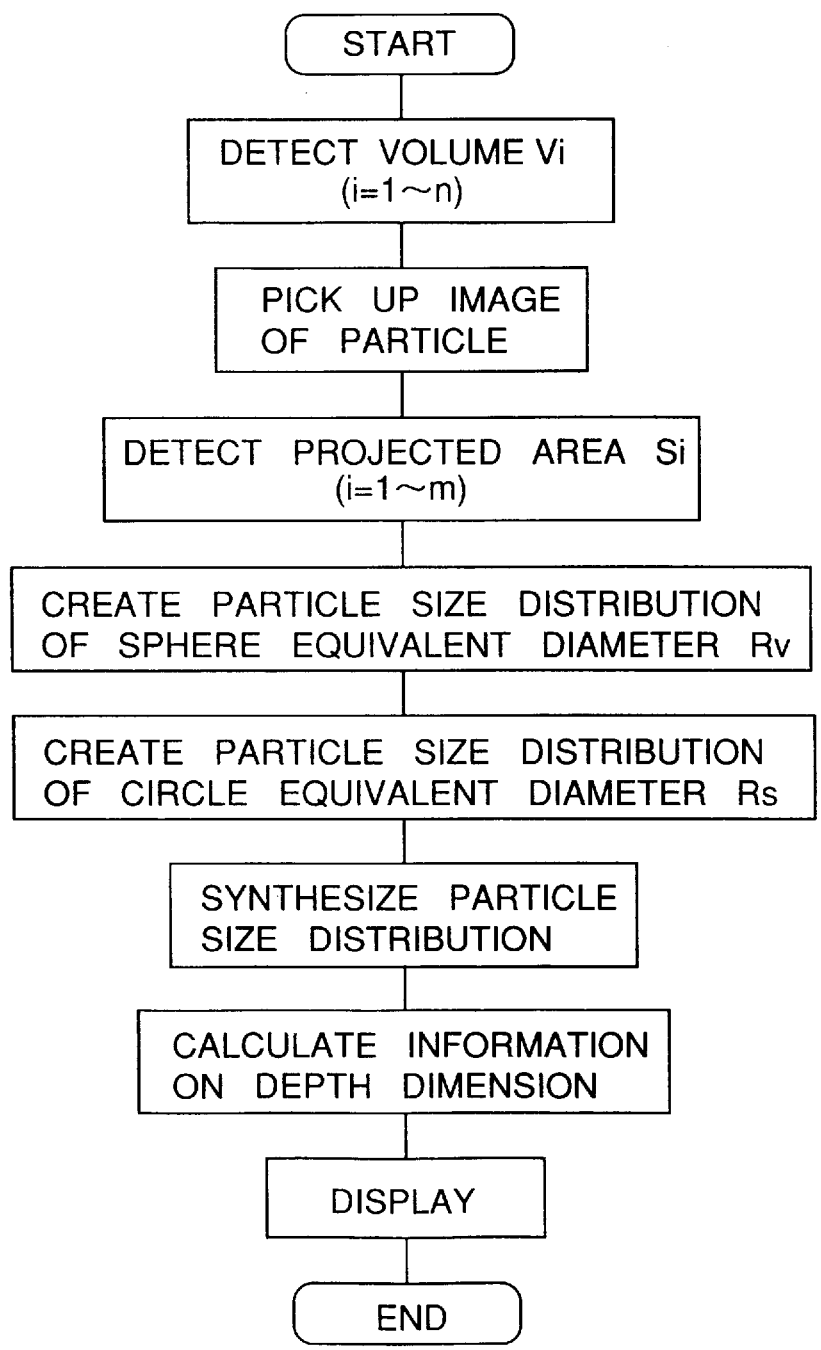
FIG. 5 is a flowchart showing procedure according to the embodiment of the present invention.
Figure 6:
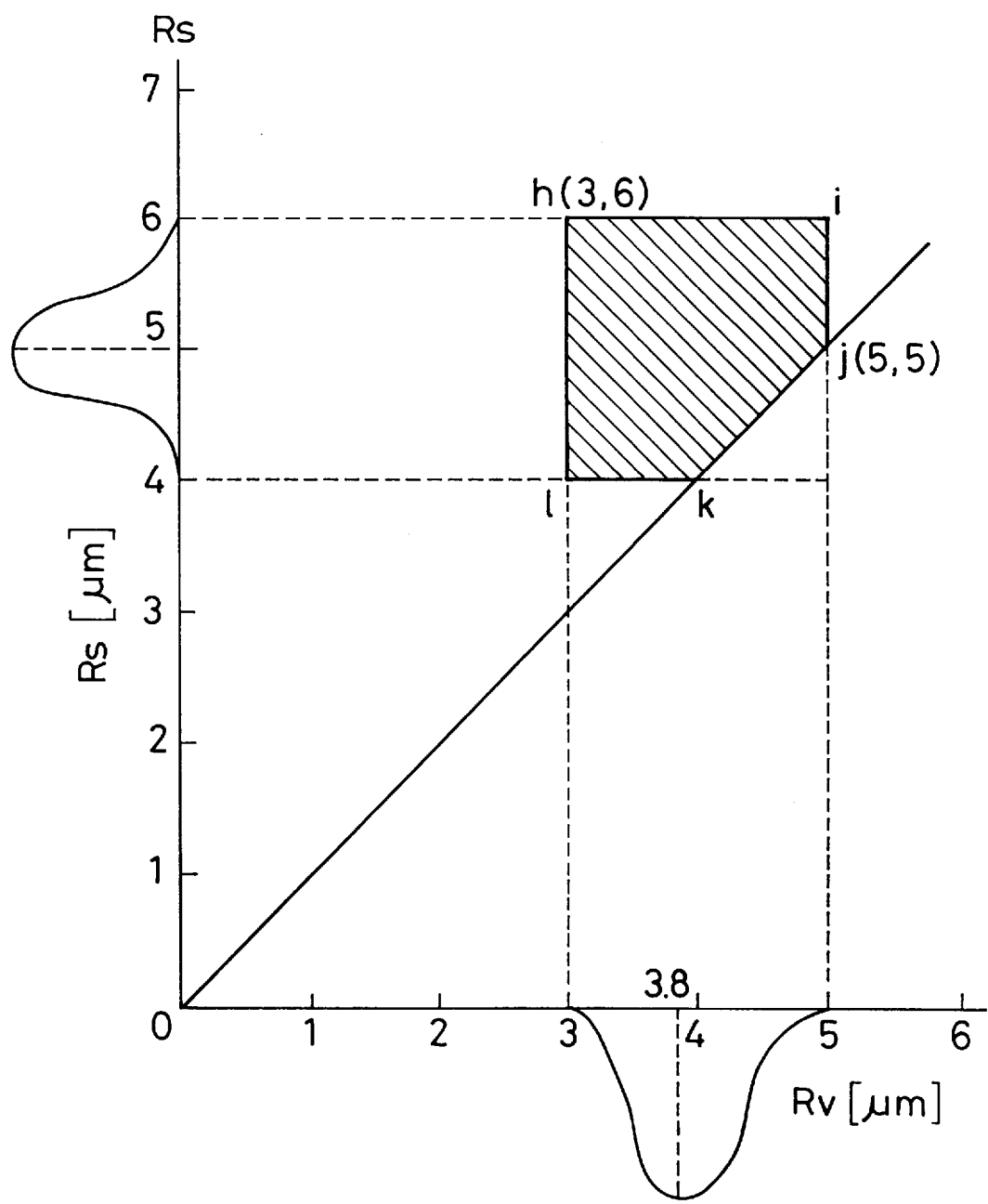
FIG. 6 is a graph showing a comparison between particle size distribution data according to the embodiment of the present invention.

Procedure of measurement is shown in a flowchart of FIG. 5. The number of particles having a volume Vi is 125000, and that of the particles having a projected area Si is 60000. FIG. 6 shows a particle size distribution for a circle equivalent diameter Rs and a sphere equivalent diameter Rv which are obtained by the measurement.

More specifically, Rs is distributed between 4 to 6 μm and has a mean value of 5 μm, and Rv is distributed between 3 to 5 μm and has a mean value of 3.8 μm.

In FIG. 6, coordinates of points h and j are (3, 6) and (5, 5).

If the coordinates of the points j and h are substituted for the equation (3), 2a has values of 5 and 0.75 so that a depth dimension has a maximum value of 5 μm and a minimum value of 0.75 μm.

If Rs=5 and Rv =3.8 are substituted for the equation (3), 2a=2.2 is obtained and the depth dimension has a mean value of 2.2 μm.

Figure 7:
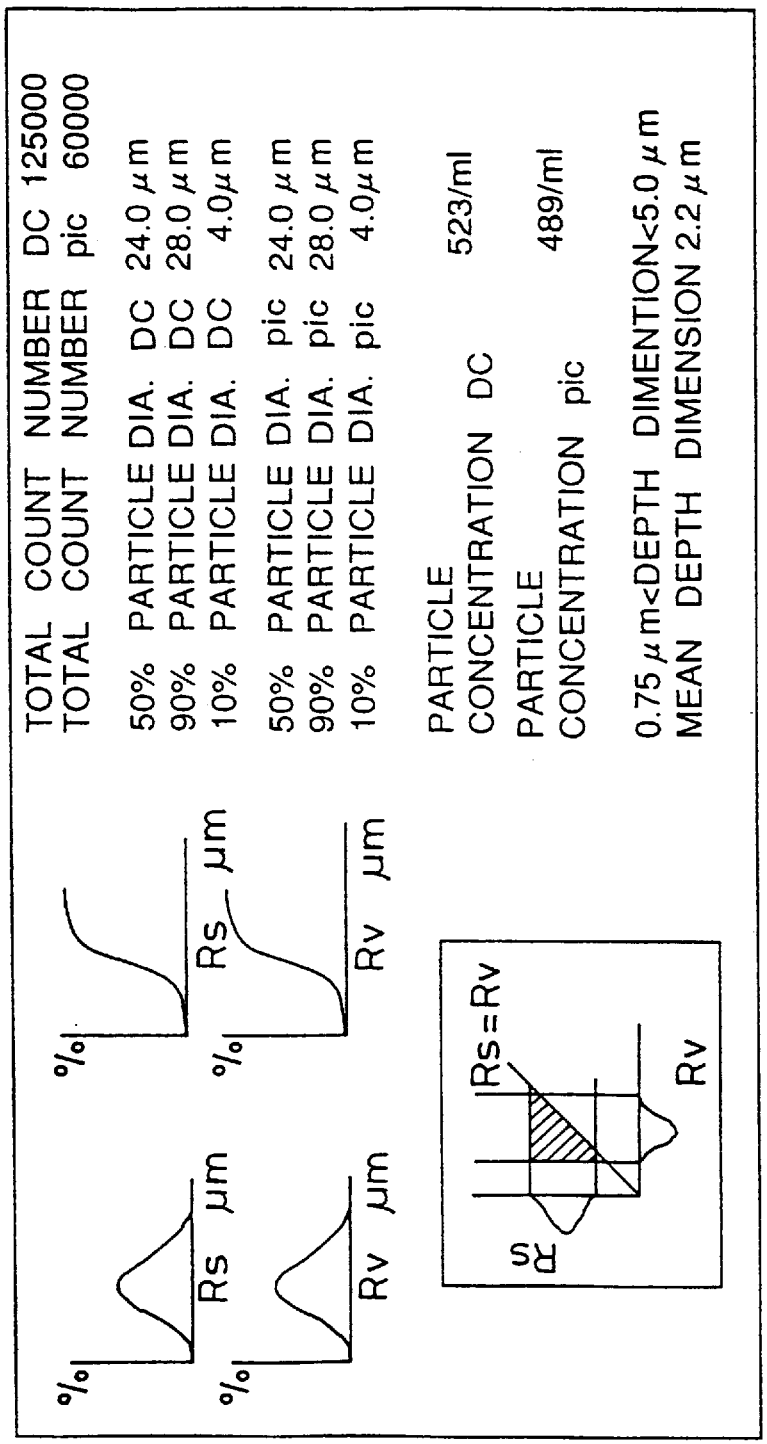
FIG. 7 is a chart showing examples of outputs according to the embodiment of the present invention.
Figure 8:
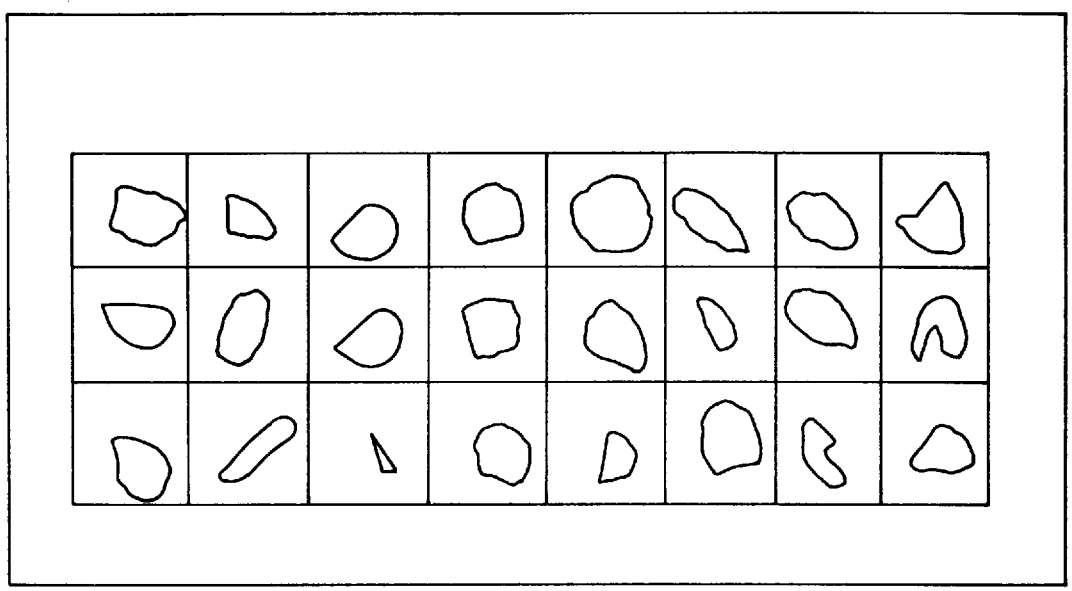
FIG. 8 is a diagram showing examples of outputs according to the embodiment of the present invention.

FIG. 7 shows each distribution data and calculated values which are outputted from the output section 30. FIG. 8 shows particle images outputted from the output section 30.

In FIG. 7, "DC" denotes data which is based on a particle volume obtained from a resistance detecting section 16, and "pic" denotes data which is based on particle images obtained from a video camera 18a.

According to the present invention, the information on the depth dimension corresponding to the particle image having a maximum projected area are obtained statistically. Consequently, shapes of a lot of particles can be analyzed easily.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What is claimed is:

1. A particle measuring apparatus, comprising:
   a first flow cell for converting a particle containing sample solution into a sample solution flow enveloped in a sheath solution;
   a resistance detecting section for detecting an electric resistance of the sample solution when the sample solution flows in the first flow cell;
   a second flow cell having a passage, said passage having an elongated cross-section for converting the particle containing sample solution into a flat flow enveloped in the sheath solution;
   an image capturing section for capturing an image of the flat flow from a wider side of said passage to obtain a particle image when the sample solution flows in said passage;
   an analyzing section for analyzing particles on the basis of the detected electric resistance and the captured particle image; and
   an output section for outputting a result obtained from the analyzing section,
   the analyzing section including:
      a first detecting section for detecting information on a volume of each particle from the detected electric resistance;
      a second detecting section for detecting information on a projected area of each particle from the captured particle image;
      a first particle size distribution calculating section for calculating a first particle size distribution on the basis of the information on the volume;
      a second particle size distribution calculating section for calculating a second particle size distribution on the basis of the information on the projected area;
      a depth calculating section for calculating information on a depth dimension of the particle on the basis of the first and second particle size distributions; and
      an output control section for causing the output section to output the information on the depth dimension and the captured particle image.

2. The particle measuring apparatus as defined in claim 1, wherein the first flow cell is incorporated with the second flow cell in series.

3. The particle measuring apparatus as defined in claim 1, wherein the first particle size distribution is a particle size distribution in which a sphere equivalent diameter of the particle is regarded as a particle size, and the second particle size distribution is a particle size distribution in which a circle equivalent diameter of the particle is regarded as a particle size.

4. The particle measuring apparatus as defined in claim 1, wherein the depth calculating section calculates the information on the depth dimension of the particle on the assumption that the particle is ellipsoidal and the captured particle image represents a maximum projected area.

5. The particle measuring apparatus as defined in claim 1, wherein the depth calculating section compares the first particle size distribusion with the second particle size distribution to calculate maximum, minimum and mean values of the depth dimension as the information on the depth dimension.

6. The particle measuring apparatus as defined in claim 1, wherein the depth calculating section calculates, as the information on the depth dimension, a maximum value of the depth dimension from a maximum particle size in the first particle size distribution, a minimum value of the depth dimension from a maximum particle size in the second particle size distribution, and a mean value of the depth dimension from a mean particle size in the first and second particle size distributions.

7. The particle measuring apparatus as defined in claim 1, wherein the depth calculating section assumes that the particle is ellipsoidal to calculate a diameter of an ellipsoidal particle as the depth dimension of the particle on the basis of the first and second particle size distributions.

8. The particle measuring apparatus as defined in claim 7, wherein the diameter of the ellipsoidal particle is a minimum diameter of the ellipsoid particle.

9. The particle measuring apparatus as defined in claim 1, wherein the depth calculating section assumes that the particle is ellipsoidal and a minimum diameter of the ellipsoidal particle represents the depth dimension to calculate, as the information on the depth dimension, a maximum value of the depth dimension from a maximum particle size in the first particle size distribution, a minimum value thereof from the maximum particle size in the second particle size distribution, and a mean value thereof from a mean value in the first and second particle size distributions.

10. The particle measuring apparatus as defined in claim 1, further comprising:

a calculating section for calculating a cumulative particle size distribution from the information on the volume and the information on the projected area, whereby the output section is caused to output, as the information on the depth dimension, the particle sizes whose cumulative particle size distributions have 10%, 50%, and 90% values.

11. The particle measuring apparatus as defined in claim 1, wherein the particle to be analyzed is carbon.

12. The particle measuring apparatus of claim 1, wherein said passage has a rectangular cross-section.

13. The particle measuring apparatus of claim 1, wherein said image capturing section includes a video camera.

* * * * *